United States Patent
Chang et al.

(10) Patent No.: US 12,256,717 B2
(45) Date of Patent: Mar. 25, 2025

(54) METHOD AND SYSTEM FOR SCANNING ANIMAL AND COMPUTER DEVICE

(71) Applicant: WUHAN UNITED IMAGING LIFE SCIENCE INSTRUMENT CO., LTD, Wuhan (CN)

(72) Inventors: Ying Chang, Wuhan (CN); Cheng-Yuan Peng, Wuhan (CN); Li Chen, Wuhan (CN); Hai-Liang Ke, Wuhan (CN)

(73) Assignee: WUHAN UNITED IMAGING LIFE SCIENCE INSTRUMENT CO., LTD, Wuhan (CN)

( * ) Notice: Subject to any disclaimer, the term of this patent is extended or adjusted under 35 U.S.C. 154(b) by 0 days.

(21) Appl. No.: 18/217,134

(22) Filed: Jun. 30, 2023

(65) Prior Publication Data

US 2023/0337638 A1 Oct. 26, 2023

Related U.S. Application Data

(63) Continuation of application No. PCT/CN2021/117615, filed on Sep. 10, 2021.

(30) Foreign Application Priority Data

Dec. 31, 2020 (CN) .......................... 202011633122.6
Dec. 31, 2020 (CN) .......................... 202011636936.5
Dec. 31, 2020 (CN) .......................... 202011636941.6

(51) Int. Cl.
*A01K 29/00* (2006.01)
*A61B 5/00* (2006.01)
*A61B 5/107* (2006.01)

(52) U.S. Cl.
CPC .......... *A01K 29/005* (2013.01); *A61B 5/1072* (2013.01); *A61B 5/448* (2013.01)

(58) Field of Classification Search
CPC ...... A01K 29/005; A61B 5/1072; A61B 5/448
(Continued)

(56) References Cited

U.S. PATENT DOCUMENTS 4,745,472 A * 5/1988 Hayes .................. A01K 29/005
356/396
5,339,815 A * 8/1994 Liu .......................... G06T 7/41
600/443

(Continued)

FOREIGN PATENT DOCUMENTS

AU 2015101963 A4 8/2019
CN 101808577 A 8/2010
(Continued)

OTHER PUBLICATIONS

European Search Report (EP Application No. 21913205.7), dated May 21, 2024, 11 pages.
(Continued)

*Primary Examiner* — Kerri L McNally

(57) ABSTRACT

The application discloses a method, apparatus and system for scanning an animal. The method includes obtaining a species of an animal to be scanned, identifying a type of an animal cabin where the animal to be scanned is located, and determining whether the species of the animal to be scanned matches the type of the animal cabin, determining and presenting a corresponding scanning protocol that matches the species of the animal to be scanned if the species of the animal to be scanned matches the type of the animal cabin, and perform a scan according to the corresponding scanning protocol, or according to a user-defined scanning protocol.

20 Claims, 7 Drawing Sheets

(58) Field of Classification Search
USPC .................................................. 340/573.3
See application file for complete search history.

(56) References Cited

U.S. PATENT DOCUMENTS

| | | | | |
|---|---|---|---|---|
| 5,483,441 | A | * | 1/1996 | Scofield .............. A01K 1/0613 |
| | | | | 382/110 |
| 5,576,949 | A | * | 11/1996 | Scofield .................... G06T 7/60 |
| | | | | 702/179 |
| 10,398,316 | B1 | | 9/2019 | Betts-Lacroix et al. |
| 2007/0239034 | A1 | * | 10/2007 | Knoche ................. G02B 27/40 |
| | | | | 359/210.1 |
| 2008/0260220 | A1 | * | 10/2008 | Djeziri ................... G06V 10/24 |
| | | | | 382/128 |
| 2012/0027167 | A1 | | 2/2012 | O'Brien et al. |
| 2014/0029808 | A1 | * | 1/2014 | Lee ....................... G06V 40/10 |
| | | | | 382/110 |
| 2016/0125276 | A1 | | 5/2016 | Spicola, Sr. et al. |
| 2018/0049695 | A1 | | 2/2018 | Hector, Jr. |
| 2018/0160649 | A1 | * | 6/2018 | Hicks ..................... A01K 7/02 |
| 2019/0166823 | A1 | * | 6/2019 | Dick ................ G06F 18/24133 |

FOREIGN PATENT DOCUMENTS

| | | |
|---|---|---|
| CN | 102512195 A | 6/2012 |
| CN | 103056864 A | 4/2013 |
| CN | 103815924 A | 5/2014 |
| CN | 104071662 A | 10/2014 |
| CN | 103098754 B | 1/2015 |
| CN | 105704380 A | 6/2016 |
| CN | 107909046 A | 4/2018 |
| CN | 107920211 A | 4/2018 |
| CN | 109051634 A | 12/2018 |
| CN | 109464155 A | 3/2019 |
| CN | 109480882 A | 3/2019 |
| CN | 209203616 U | 8/2019 |
| CN | 110471067 A | 11/2019 |
| CN | 111406733 A | 7/2020 |
| ES | 1160733 U | 7/2016 |
| JP | 2014064776 A | 4/2014 |
| KR | 20140052125 A | 5/2014 |
| KR | 20140052126 A | 5/2014 |
| WO | 2015036495 A1 | 3/2015 |
| WO | 2016128965 A2 | 8/2016 |

OTHER PUBLICATIONS

Chinese Office Action and Search Report (CN Application No. 2020116369416) dated Jun. 17, 2024, 9 pages.
International Search Report of PCT/CN2021/117615.
Office Action CN2020116369365 dated Aug. 28, 2024.

* cited by examiner

FIG. 6

METHOD AND SYSTEM FOR SCANNING ANIMAL AND COMPUTER DEVICE

CROSS REFERENCE TO RELATED APPLICATIONS

The present application is a continuation application of International Patent Application No. PCT/CN2021/117615 filed on Sep. 10, 2021, which claims priority to Chinese Patent Application No. 202011636936.5, entitled "METHOD, APPARATUS AND SYSTEM FOR IMAGE SCANNING BASED ON ANIMAL RECOGNITION", filed on Dec. 31, 2020, Chinese Patent Application No. 202011636941.6, entitled "METHOD, APPARATUS AND SYSTEM FOR SCANNING ANIMAL", filed on Dec. 31, 2020, and Chinese Patent Application No. 202011633122.6, entitled "ANIMAL IMAGING DEVICE AND FOCUSING METHOD OF SURVEILLANCE CAMERA THEREOF, AND VIDEO SURVEILLANCE METHOD", filed on Dec. 31, 2020, all of which are hereby incorporated by reference in their entireties.

TECHNICAL FIELD

This application relates to the technical field of medical imaging, particularly to a method, apparatus and system for scanning an animal.

BACKGROUND

Before scanning a preclinical image of an animal, a corresponding scanning protocol needs to be set first. After the scanning protocol is determined, the animal is positioned according to an optimal scanning position corresponding to the scanning protocol and then scanned. When positioning an animal, in order to prevent the animal from moving around, the animal is usually anesthetized and then the animal's body position is fixed.

At present, human recognition is used to determine animal species. The type of Animal cabin is also determined based on the experience of the operator. Before scanning, it is necessary to manually enter basic animal information. When selecting or setting the scanning protocol, manual selection is usually used. This method is less efficient, prone to errors, and is not suitable for inexperienced operators.

SUMMARY

According to some embodiments of the present application, a method for scanning an animal is provided. The method includes obtaining a species of an animal to be scanned, identifying a type of an animal cabin where the animal to be scanned is located and determining whether the species of the animal to be scanned matches the type of the animal cabin, determining and presenting a corresponding scanning protocol that matches the species of the animal to be scanned if the species of the animal to be scanned matches the type of the animal cabin, and performing a scan according to the corresponding scanning protocol, or according to a user-defined scanning protocol.

In an embodiment, the method further includes obtaining an image of the animal to be scanned, and obtaining the species of the animal to be scanned according to the image of the animal to be scanned, and/or monitoring the animal to be scanned in real time according to the image of the animal to be scanned.

In an embodiment, before performing the scan according to the user-defined scanning protocol, the method further includes determining whether the user-defined scanning protocol matches the species of the animal to be scanned, and if not, prompting to modify the user-defined scanning protocol.

In an embodiment, the method further includes obtaining a physiological signal and a real-time image of the animal to be scanned, determining whether the animal to be scanned is alive according to the physiological signal and the real-time image, and if not, outputting an animal sample change reminder.

In an embodiment, obtaining the species of the animal to be scanned includes setting physiological signal ranges for different species of animals and establishing a physiological signal database, and determining an animal species in the physiological signal database that matches the physiological signal, and obtaining the species of the animal to be scanned.

In an embodiment, obtaining the species of the animal to be scanned includes obtaining a body length parameter of the animal by recognizing the image, obtaining a weight parameter of the animal to be scanned, comparing the obtained body length parameter and the obtained body weight parameter with pre-stored standard body lengths and pre-stored standard body weights respectively, and determining the animal species information.

In an embodiment, the method further includes, after obtaining the image of the animal to be scanned, obtaining a hair parameter of the animal, and determining the animal species information according to the hair parameter, the body length parameter, and the weight parameter of the animal. The hair parameter includes at least one of a hair length, a hair diameter, and a hair color.

In an embodiment, obtaining the body length parameter of the animal by recognizing the image includes providing a ruler with markings on either side of the animal and obtaining the body length parameter by recognizing the markings of the ruler, and/or marking characteristic points on an animal body and determining the body length parameter by recognizing the characteristic points.

In an embodiment, obtaining the weight parameter of the animal to be scanned includes obtaining a plurality of body weight values of the animal to be scanned, and obtaining the body weight parameter of the animal to be scanned based on the plurality of body weight values.

In an embodiment, the method further includes determining whether a specified part of an animal body is shaved or not and whether an electrode sheet is attached to the specified part according to the image of the animal to be scanned to select a respiratory-electrocardiogram protocol.

In an embodiment, identifying the type of the animal cabin where the animal to be scanned is located, and determining whether the species of the animal to be scanned matches the type of the animal cabin includes the type of the animal cabin including a type of corresponding animal beds and a number of the animal beds, obtaining an occupancy of each animal bed in the animal cabin, identifying the species of the animal to be scanned on the occupied animal bed, determining whether the species of the animal to be scanned is the same as the type of the animal bed, and if yes, determining that the species of the animal to be scanned matches the type of the animal cabin, otherwise, determining that the species of the animal to be scanned does not match the type of the animal cabin.

In an embodiment, before performing the scan according to the corresponding scanning protocol, or according to the user-defined scanning protocol, the method further includes obtaining an optimal scanning position corresponding to the scanning protocol, obtaining the image of the animal to be scanned, recognizing characteristic points in the image as actual characteristic points, and obtaining an actual body position of the animal to be scanned according to coordinates of a plurality of actual characteristic points, the scanning position includes scanning characteristic points in one-to-one correspondence with the plurality of actual characteristic points, calculating a sum of the distances between the actual characteristic points and the corresponding scanning characteristic points as a distance similarity, connecting any two actual characteristic points to obtain a plurality of actual characteristic lines, connecting any two scanning characteristic points to obtain a plurality of scanning characteristic lines, calculating a sum of angles between the actual characteristic lines and the corresponding scanning characteristic lines as an angle similarity, calculating a weighted sum of the distance similarity and the angle similarity to obtain a similarity between the actual body position and the scanning position, and determining whether the similarity is larger than a preset threshold, and if not, outputting a body position adjustment parameter guiding body position adjustment until the similarity between the actual body position and the scanning position is larger than the preset threshold, before scanning.

In an embodiment, before the obtaining the image of the animal to be scanned, the method further includes obtaining a distance between the animal cabin and a camera, and adjusting a focal length of the camera according to the distance to realize focusing of the camera.

In an embodiment, obtaining the distance between the animal cabin and the camera includes obtaining an initial distance between the animal cabin and the camera, obtaining real-time data of an encoder of a driving device of the animal cabin and obtaining a real-time travel distance of the animal cabin according to the real-time data of the encoder, the driving device of the animal cabin is configured to drive the animal cabin to move, and calculating a real-time distance between the animal cabin and the camera according to the initial distance and the real-time travel distance.

According to some embodiments of the present application, an animal scanning apparatus is provided. The animal scanning apparatus includes a first obtaining unit configured for obtaining a species of an animal to be scanned, a determining unit configured for identifying a type of an animal cabin where the animal to be scanned is located and determining whether the species of the animal to be scanned matches the type of the animal cabin, a matching unit configured for matching and presenting a corresponding scanning protocol according to the species of the animal to be scanned if the species of the animal to be scanned matches the type of the animal cabin, and a scanning unit configured for performing a scan according to the corresponding scanning protocol, or according to a user-defined scanning protocol.

According to some embodiments of the present application, an animal scanning system is provided. The animal scanning system includes an animal scanning apparatus according to the second aspect. The animal scanning system further includes an animal cabin, an image obtaining device, and a physiological signal detecting device. The animal cabin is arranged on a bed body and configured to place an animal to be scanned. The image obtaining device is configured to obtain an image of the animal to be scanned. The physiological signal detecting device is configured to obtain a physiological signal of the animal to be scanned. The animal scanning apparatus is configured to perform a scan on the animal to be scanned.

In an embodiment, the animal scanning system further includes a light source and an animal imaging device body. The animal imaging device body has a scanning hole, the animal cabin is able to move along an axial direction of the scanning hole, and the light source is fixedly arranged on the animal imaging device body.

In an embodiment, the image obtaining device is arranged on the animal cabin and/or on the animal imaging device body.

BRIEF DESCRIPTION OF THE DRAWINGS

In order to illustrate more clearly the embodiments of the present application or the technical solutions in the prior art, the accompanying drawings required in the description of the embodiments or the prior art will be described briefly below, and it will be apparent that the accompanying drawings described below are merely the embodiments of the present application and other accompanying drawings may be obtained from the disclosed drawings by one of ordinary skill in the art without making creative labor.

FIG. 6 is a diagram of an animal cabin registration information input interface according to a method for scanning an animal according to some embodiments of the present application;

REFERENCE NUMERALS

1: Camera; 2: Animal cabin; 3: Light source; 4: Animal imaging device body; 5 Animal scanning device; 6:

Animal cabin; 61: Data interface; 7: Image obtaining device; 8: Physiological signal detecting device.

DETAILED DESCRIPTION

The technical solutions in the embodiments of this application will be clearly and completely described below in conjunction with the accompanying drawings in the embodiments of this application. Obviously, the described embodiments are only a part of the embodiments of the present application, and not all of them. Based on the embodiments in the present application, all other embodiments obtained by a person of ordinary skill in the art without making creative labor fall within the scope of protection of the present application.

Figure 1:
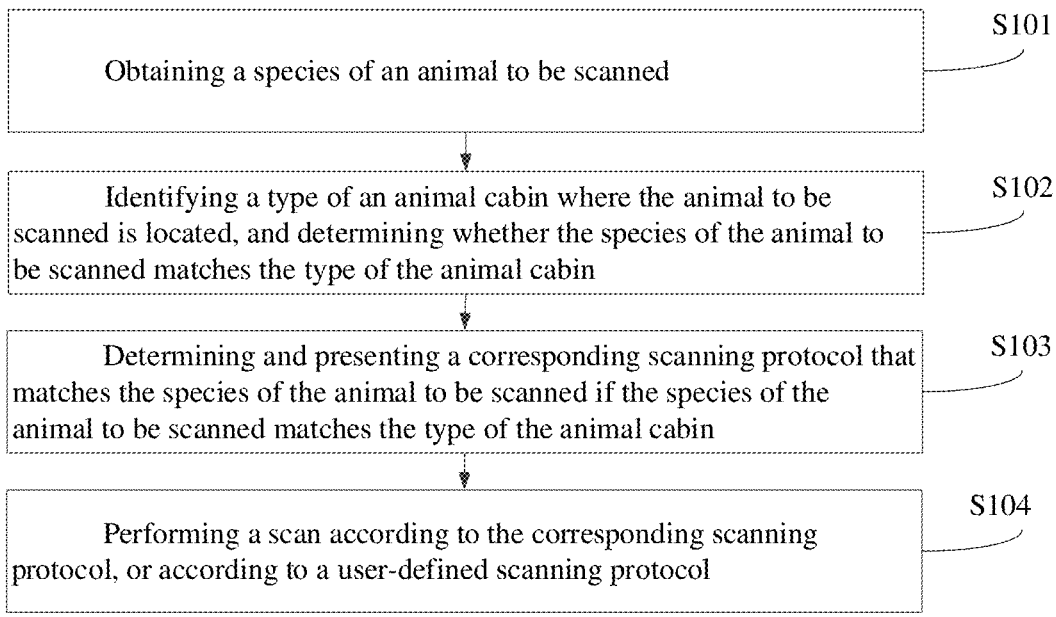
FIG. 1 is a schematic flow chart of a method for scanning an animal according to some embodiments of the present application.

FIG. 1 is a flow chart of a method for scanning an animal according to some embodiments of the present application. The method includes the following steps S101-S104.

In the step S101, a species of an animal to be scanned is obtained.

In some embodiments, a scanning device can obtain an image of the animal to be scanned and obtain a species of the animal to be scanned based on the image of the animal to be scanned. In some embodiments, the scanning device may capture an image of the animal to be scanned through a camera such as a video camera or a high-definition camera.

In the step S102, a type of an animal cabin where the animal to be scanned is located is identified, and whether the species of the animal to be scanned matches the type of the animal cabin is determined.

In some embodiments, data such as the scanned image of the animal to be scanned is transmitted to a scanning terminal outside the animal cabin during scanning. A data transmission interface is provided on the animal cabin, and the type of the animal cabin can be identified through the type of the data transmission interface and the type of data transmitted. After the identification of the animal species and the type of the animal cabin is completed, the matching determination between the animal cabin and the animal can be completed. If the animal cabin and the animal do not match, a user is prompted to replace the animal, and if the animal cabin matches the animal, a corresponding scanning protocol that matches the animal species can be determined.

In the step S103, a corresponding scanning protocol that matches the species of the animal to be scanned is determined and presented, if the species of the animal to be scanned matches the type of the animal cabin.

In some embodiments, the selection of scanning protocols may be implemented in either an auto-match or a user-defined manner. The automatic matching of the scanning protocol can be realized by establishing a scanning protocol pool. A corresponding scanning protocol is established for each scanning area of each animal, and the scanning protocol can be automatically matched in the scanning protocol pool according to the species of the animal to be scanned and the scanning area. If a user feels that the scanning protocol obtained by automatic matching is incorrect or the matching precision is not high, or if an experienced operator thinks that the scanning protocol obtained by automatic matching needs to be modified, they can make user-defined settings for the scanning protocol.

In the step S104, a scan is performed according to the corresponding scanning protocol or according to a user-defined scanning protocol.

Once the scanning protocol has been determined, the subsequent scanning process can be performed. In some embodiments, the scanning device may perform the scan according to the scanning protocol that matches the species of the animal to be scanned or perform the scan according to the user-defined scanning protocol.

According to some embodiments of the present application, identification of animal species is performed prior to performing an animal scan in order to automatically match the scanning protocol according to the animal species. When performing scanning protocol matching, there is no need to manually enter the basic animal information. The matched scanning protocol is presented to the user. If the user is not satisfied with the matched scanning protocol, the scanning protocol can be user-defined, thereby making the selection of scanning protocol more flexible. At the same time, before matching the scanning protocol, the degree of match between the animal and the animal cabin is automatically determined, and the subsequent scanning protocol determination and scanning process are performed after ensuring that the animal matches the animal cabin, so as to further improve the automation degree of the scanning process.

Figure 2:
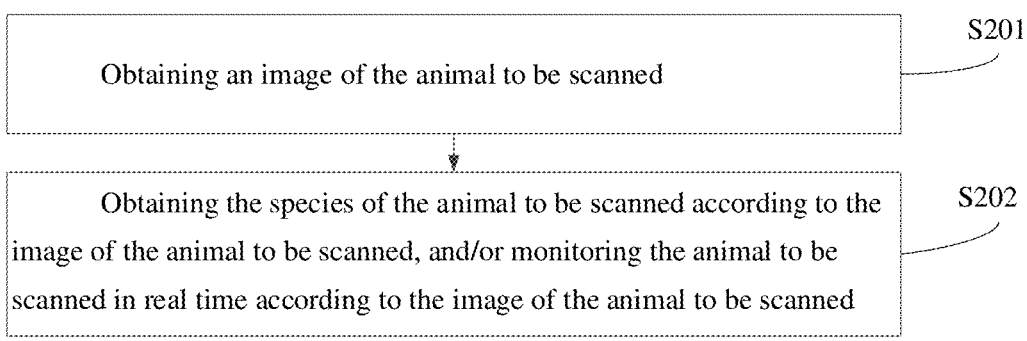
FIG. 2 is a schematic flow chart of a method for scanning an animal according to some embodiments of the present application.

According to some embodiments of the present application, prior to scanning and/or during scanning, the image of the animal to be scanned is obtained. The species of the animal to be scanned is obtained according to the image of the animal to be scanned, and/or the animal to be scanned is monitored in real time through the image of the animal to be scanned. The scanning device may also monitor the animal to be scanned in real time during scanning of the animal to be scanned. In some embodiments, as shown in FIG. 2, a method for scanning an animal includes the following steps S201-S202.

In the step S201, an image of the animal to be scanned is obtained.

In some embodiments, a scanning device obtains the image of the animal to be scanned. In some embodiments, the scanning device may obtain the image of the animal to be scanned through its own camera or may obtain the image of the animal to be scanned from a camera in communication connection with the scanning device.

In the step S202, the species of the animal to be scanned is obtained, and/or the animal to be scanned is monitored in real time according to the image of the animal to be scanned.

In an application where the species of the animal to be scanned is obtained based on the image of the animal to be scanned, in some embodiments, the scanning device may obtain a body length parameter of the animal to be scanned based on the image of the animal to be scanned, and the species of the animal to be scanned based on the body length parameter of the animal to be scanned. It should be noted that the image of the animal to be scanned here is a still image of the animal to be scanned. The still image can be taken by an optical camera with a camera before scanning, or by a high-definition camera device with a camera. In an application where the animal to be scanned is monitored in real time according to the image of the animal to be scanned, in some embodiments, the scanning device may monitor the animal to be scanned in real time according to the image of the animal to be scanned. It should be noted that the image of the animal to be scanned here is a real-time image of the animal to be scanned. The real-time image can be obtained in real time by a high-definition camera device with a camera during scanning.

In this embodiment, the species of the animal to be scanned can be quickly obtained according to the image of the animal to be scanned, and the animal to be scanned can be monitored by real-time video during the animal imaging experiment according to the image of the animal to be scanned, so that an operator can obtain the conditions of the animal in the animal cabin in real time.

Before performing the scan according to the user-defined scanning protocol, it is also necessary to determine whether the user-defined scanning protocol matches the species of the animal to be scanned. Based on the embodiments described above, in an embodiment, the method further includes determining whether the user-defined scanning protocol matches the species of the animal to be scanned, and if not, prompting to modify the user-defined scanning protocol.

In some embodiments of the present application, after the scanning protocol is matched, the scanning protocol and a corresponding optimal scanning position may be output and displayed at a scanning terminal for viewing by the user and directing the positioning of the animal. After the scanning terminal displays the scanning protocol and the corresponding optimal scanning position, the user can manually check the matched scanning protocol and scanning position at the scanning terminal. If the user feels that the result of automatic matching is not suitable, it is possible not to choose the automatically recommended scanning protocol and the optimal scanning position, but to manually set the scanning protocol and the scanning position, or modify the matched scanning protocol and the scanning position. The scanning position is displayed by a body model diagram in some embodiments. When the body model diagram of an animal is displayed at the scanning terminal and the user moves the mouse to a certain position on the body model diagram of the animal, the corresponding body part on the body model diagram will be automatically highlighted, and the scanning protocols matching the current body model diagram will be displayed in a list for the user to select. The optimal scanning protocol and the optimal scanning position recommended by the automatic matching will also be highlighted, which is convenient for the operator to compare and modify. For different species of animals, different body model diagrams and scanning protocols are available. For example, whole-body scanning, brain scanning, etc., are available for mice, and single/multi-bed, chest, brain scanning, etc., are available for dogs.

In this embodiment, the scanning device determines whether the user-defined scanning protocol matches the species of the animal to be scanned or not, and prompts the user to modify the user-defined scanning protocol in the case that the user-defined scanning protocol does not match the species of the animal to be scanned, to ensure the accuracy of the scanning protocol for scanning the animal to be scanned.

Figure 3:
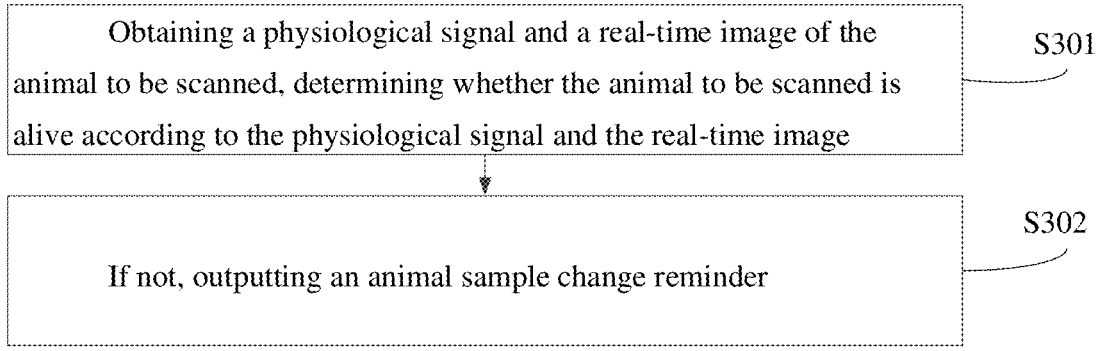
FIG. 3 is a schematic flow chart of a method for scanning an animal according to some embodiments of the present application.

In some embodiments of the present application, as shown in FIG. 3, the method for scanning an animal includes the following steps S301-S302:

In the step S301, a physiological signal and a real-time image of the animal to be scanned are obtained, and whether the animal to be scanned is alive is determined according to the physiological signal and the real-time image.

In some embodiments of the present application, for a multi-animal cabin that can accommodate a plurality of animals to be scanned at the same time, before or during the scanning process of the animal to be scanned, the physiological signal of the animal to be scanned and the real-time image of the animal can be combined to determine the survival status of the animal, so as to avoid any invalid scan caused by the fact that some animals have died due to intolerance of anesthetic drugs or other reasons and the user does not find them in time. In an embodiment of the present application, if the physiological signal does not exist and the animal to be scanned is not recognized in the real-time image of the animal, it is determined that the animal is not placed in the scanning area, and if the physiological signal exists and the animal to be scanned can be recognized in the real-time image, it is determined that the animal has been placed in the scanning area and survives. If the physiological signal does not exist, but the animal to be scanned can be recognized in the real-time image of the animal, it is determined that the animal is dead. The scanning process can be continued under the condition that the animal to be scanned is in a living state. It should be understood that, in some embodiments in which, for example, an animal cabin can accommodate only a single animal in a single scan, it is also possible to determine whether the animal to be scanned is alive by using the physiological signals or the real-time image alone or to determine whether the animal to be scanned is alive by obtaining physiological signals from the real-time image (e.g., obtaining respiratory signals according to the real-time image).

In the step S302, if not, an animal sample change reminder is output.

Specifically, if the scanning device determines the death of the animal to be scanned according to the physiological signals of the animal to be scanned and the real-time image, the animal sample change reminder is outputted to timely replace the dead animal sample.

In this embodiment, by obtaining physiological signals and the real-time image of the animal to be scanned, the scanning device can determine whether the animal to be scanned is alive according to the physiological signals and the real-time image of the animal to be scanned, so as to avoid any invalid scan caused by the fact that some animals has died due to intolerance of anesthetic drugs or other reasons and the user does not find them in time.

In the above-mentioned application for obtaining the species of the animal to be scanned, in some embodiments, the species of the animal to be scanned can be obtained by image recognition directly through the obtained image. In some embodiments, the species of the animal to be scanned can be obtained according to the physiological signals of the animal to be scanned, or according to a body length parameter and a weight parameter of the animal to be scanned.

Figure 4:
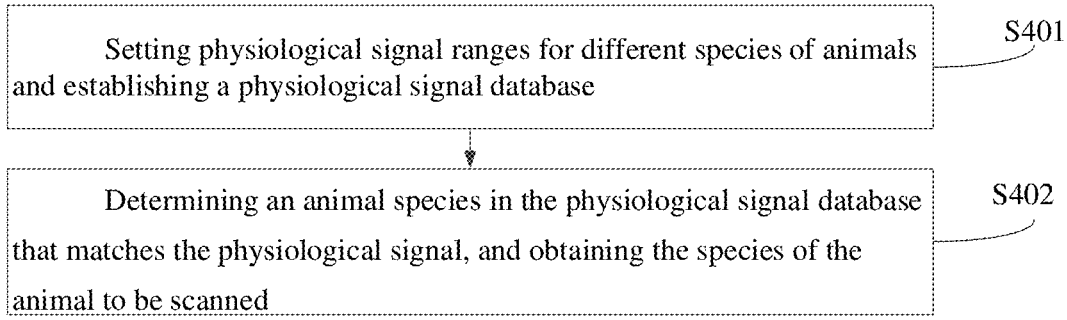
FIG. 4 is a schematic flow chart of a method for scanning an animal according to some embodiments of the present application.

In some embodiments, as shown in FIG. 4, the above step S101 includes the following steps S401-S404.

In the step S401, the physiological signal ranges for different animals are set, and a physiological signal database is established.

In some embodiments, the animal species is identified by physiological signals. Firstly, a physiological signal database is established, for example, the physiological signal database includes three animals, i.e., a mouse, a rat, and a rabbit. The physiological signal range of the mouse is set as follows: the body temperature is 37-39° C., the heart rate is 470-780 times/minute, and the weight is 15-25 grams. The physiological signal range of the rat is set as follows: the body temperature is 37.8-38.8° C., the heart rate is 260-450 times/minute, and the weight is 180-500 grams. The physiological signal range of the rabbit is set as follows: the body temperature is 38.5-39.5° C., the heart rate is 180-250 times/minute, and the weight is 500-2000 grams.

In the step S402, an animal species in the physiological signal database that matches the physiological signal is determined and the species of the animal to be scanned is obtained.

In some embodiments, after the establishment of the physiological signal database, the physiological signals of the animal to be scanned are obtained, and a matching process is performed on the physiological signals of the animal to be scanned based on the physiological signal database, to determine the animal species in which each physiological signal of the animal to be scanned is in a corresponding physiological signal range. As such, the species of the animal to be scanned is obtained. If there are more than one animal species matching the animal to be scanned (i.e., each physiological signal is in the corresponding physiological signal range), the animal species with the highest matching degree is selected as the final species of the animal to be scanned. The matching degree can be calculated by the following equation:

$$P_j = \sum_{i=1}^{N} |x_i - \overline{x}_{ij}|/\overline{x}_{ij}$$

where $P_j$ is a matching degree between the animal to be scanned and the j-th animal species, $x_i$ is a value of the i-th physiological signal of the animal to be scanned, and $\overline{x}_{ij}$ is a physiological signal average of the i-th physiological signal of the j-th animal species which can be equal to an average of the upper and lower limits of the corresponding physiological signal range.

If the animal species matching the animal to be scanned is zero, the animal species with the largest number of items matching the physiological signals of the animal to be scanned is selected as the final species of the animal to be scanned. If there are multiple animal species with the largest number of items matching the physiological signals, the animal species with the highest matching degree is selected as the final species of the animal to be scanned. The matching degree can be calculated by referring to the above equation.

In the embodiment, the identification of animal species is realized by comparing physiological signals. The comparison of physiological signals does not require setting a mark on the animal body, but rather a measuring device such as a bracelet or an anklet is arranged on the animal body, so that non-invasive identification can be realized.

Figure 5:
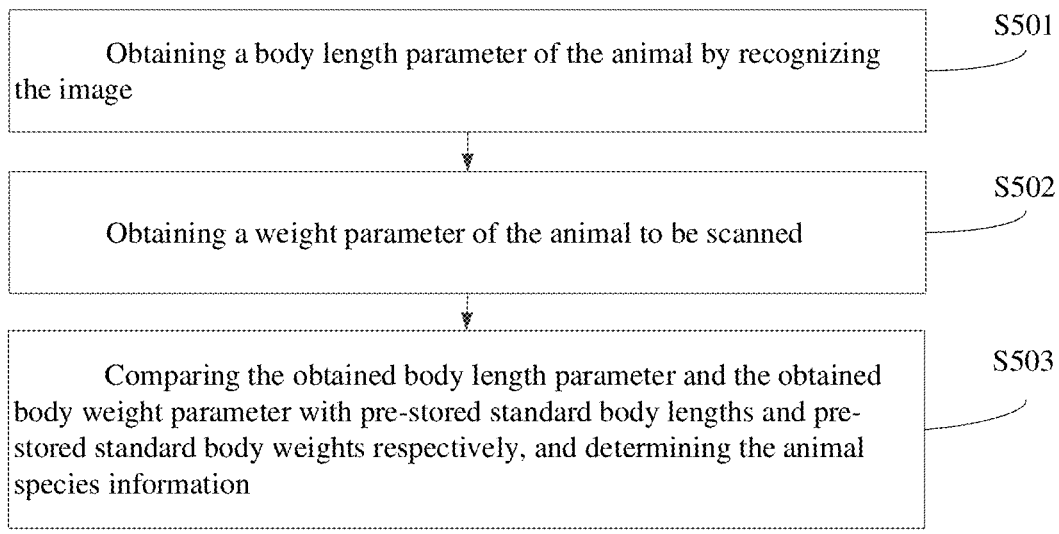
FIG. 5 is a schematic flow chart of a method for scanning an animal according to some embodiments of the present application.

In some embodiments, as shown in FIG. 5, the above step S101 includes the following steps S501-S503.

In the step S501, a body length parameter of the animal is obtained by recognizing the image.

In some embodiments, the scanning device obtains a body length parameter of the animal, i.e., the length from head to tail, by recognizing the image of the animal to be scanned.

In an embodiment of the present application, the animal to be scanned is photographed by a camera located at the animal cabin to obtain the image of the animal, which is a still image of the animal to be scanned. After recognizing the image, the body length parameter of the animal is obtained according to the image, and the body length parameter is transmitted to a terminal device with computing logic such as a server or a cloud.

In an embodiment of the present application, the method for recognizing the image to obtain the body length parameter of an animal is to arrange a ruler with markings on either side of the animal, so that after the image is formed, the body length parameter can be obtained directly by identifying the markings of the ruler. It is also possible to mark characteristic points on the body of the animal in advance. For example, a first characteristic point is set on the head of the animal, and a plurality of reflective points at equal intervals are set from the head to the tail of the animal After the image is formed, the body length parameter of the animal is determined by recognizing the number of the characteristic points.

In an embodiment, a ruler and characteristic points may also be provided at the same time to recognize the markings of the ruler and characteristic points respectively, thereby verifying the accuracy of the obtained body length parameter.

In the step S502, a weight parameter of the animal to be scanned is obtained.

Specifically, in an embodiment of the present application, the weight parameter of the animal is obtained by measuring the weight of the animal.

Alternatively, in an embodiment of the present application, the weight of the animal located in an animal cabin is read by a gravity sensor to obtain a weight parameter.

Alternatively, in another embodiment of the present application, the scanning device may also obtain the weight parameter of the animal to be scanned by following steps S1 and S22.

In the step S1, a plurality of body weight values of the animal to be scanned are obtained.

In some embodiments, after the animal is placed in the animal cabin, its breathing is accompanied by small amplitude movements, i.e., the expansion of the lungs during the breathing process drives the body to perform a slight movement, which affects the values of the weight measurement by the gravity sensor. Under the condition that the body weight of the animal is small, the measurement error caused by slight movement will account for a large proportion of the body weight. Multiple measurements, i.e., achieved by manually setting a preset time and measuring the weight of the animal once every other preset time, can improve the accuracy of body weight measurement. In an embodiment, the preset time is selected according to the respiratory frequency of the animal. Each species of animal has a different respiratory frequency, such as 30-50 beats/minute for macaques, 16-20 beats/minute for dogs, and 20-30 beats/minute for cats. Different breathing frequencies produce different small amplitude movements during breathing, i.e., the influence of small amplitude movement on a single body weight measurement value is also different. For animals with different breathing frequencies, the preset time is also different. For example, for those with high breathing frequencies, the preset time interval is reduced, and for those with low breathing frequencies, the preset time interval is increased. In an embodiment, the respiratory frequency may be detected and counted by a monitor, a breath detector, or the like.

It is to be understood that each time an animal is placed in the animal cabin, the animal is not always placed at the center of the animal cabin. In an embodiment, a pressure sensor is selected to obtain the weight parameters of the animal to be scanned, and in an embodiment, four-corner film pressure sensors are selected to carry out each weight measurement. The body weight value of the animal is simultaneously measured by four four-corner film pressure sensors around the animal, and the body weight value obtained by each measurement is the sum of the values collected by the four film pressure sensors. By using the four-corner film pressure sensor, an accurate single measurement result can be obtained regardless of whether the animal is located at the center of the animal cabin or not.

In the step S22, a weight parameter of the animal to be scanned is obtained based on a plurality of weight values.

In an embodiment of the present application, after the preset time interval is set and the body weight value is obtained multiple times, the body weight values obtained multiple times are averaged, and a result obtained is the body weight parameter of the animal That is, the body weight values obtained multiple times are added and then divided by the number of obtaining times to obtain a result that is the weight parameter of the animal. In an embodiment, the weight value is obtained at least twice.

In the step S503, the animal species information is determined by comparing the obtained body length parameter and the obtained body weight parameter of the animal with pre-stored standard body lengths and pre-stored standard body weights respectively.

In an embodiment of the present application, standard body lengths and standard body weights corresponding to a plurality of species of animals are pre-stored in a terminal device in advance. After obtaining the body length parameter and the weight parameter of the animal, the scanning device respectively compares the obtained body length parameter and the obtained weight parameter with the plurality of pre-stored standard body lengths and the standard body weights, and finds, among the plurality of pre-stored standard body lengths and the standard body weights, a group which includes a standard body length and a standard body weight equal to the obtained body length parameter and the weight parameter respectively. Namely, the standard body length and the body length parameter are consistent, and the standard body weight and the weight parameter are consistent so that the animal species corresponding to the standard body length and the standard body weight is the species of the animal in the animal cabin.

In this embodiment, the process of obtaining the body length parameter of the animal to be scanned and the body weight parameter of the animal to be scanned by recognizing the image of the animal to be scanned is relatively simple and can be realized only by performing simple identification. Thus, the obtained body length parameter and the body weight parameter of the animal can be quickly compared with the pre-stored standard body lengths and the standard body weights respectively, and the species information of the animal can be quickly determined, and the efficiency of determining the species information of the animal is improved.

Based on the above embodiment, after the image of the animal to be scanned is obtained, the hair parameter of the animal can be obtained in addition to the body length parameter of the animal when the image of the animal to be scanned is recognized. In an embodiment, the method further includes, after obtaining the image of the animal to be scanned, obtaining a hair parameter of the animal, and determining the animal species information according to the hair parameter, the body length parameter, and the weight parameter of the animal. The hair parameter includes at least one of a hair length, a hair diameter, and a hair color.

In this embodiment, when recognizing the image of the animal to be scanned, the hair parameter of the animal is obtained in addition to the body length parameter of the animal. The hair parameter includes at least one of the length of hair, the diameter of the hair, and the color of the hair. Standard hairs of a plurality of animals are also pre-stored in the terminal device, and the standard hair includes at least one of a length of the hair, a diameter of the hair, and a color of the hair. The standard hairs are compared with the hair parameter to assist in distinguishing animal species in the case that the weight parameters and the length parameters of different animals of the same family but different genera are similar.

In this embodiment, after the scanning device obtains the image of the animal to be scanned, the scanning device can also obtain the hair parameter of the animal, and the animal species information of the animal to be scanned can be determined according to the hair parameter, the body length parameter and the weight parameter of the animal, so that the animal species can be distinguished in the case that the weight parameters and the body length parameters of different animals of the same family but different genera are similar, and the accuracy of determining the animal species information can be improved.

In some embodiments of the present application, the method for scanning an animal includes determining whether a specified part of an animal body is shaved or not and whether an electrode sheet is attached to the specified part according to the image of the animal to be scanned to select a respiratory-electrocardiogram protocol.

In some embodiments, when selecting a protocol for scanning, it is first determined whether the selected protocol is related to respiratory-electrocardiogram. If related, the image of the animal to be scanned taken by the camera is first observed directly by the naked eyes or recognized automatically to identify and determine whether the specified part of the animal in the animal cabin is shaved and has an electrode sheet attached thereon. The respiratory-electrocardiogram-related protocol is performed only when the specified part is shaved and an electrode sheet is attached thereon. Otherwise, the shaving of the specified part and attaching of the electrode sheet will be performed first. If the selected protocol is not related to the respirator-electrocardiogram, the scan can be performed directly.

In this embodiment, when selecting the respiratory-electrocardiogram protocol, the scanning device identifies whether the specified part of the animal body is shaved or not and is attached with an electrode sheet through the image of the animal to be scanned, so as to ensure the safety in the process of the scanning device performing the scanning protocol and ensure a smooth scanning process.

When the scanning device identifies the type of animal case where the animal to be scanned is located, and determines whether the species of the animal to be scanned matches the type of the animal case as described above, in an embodiment, the type of the animal cabin involves a type of corresponding animal beds and a number of the animal beds. The step S102 includes: obtaining an occupancy of each animal bed in the animal cabin; identifying the species of the animal to be scanned on the occupied animal bed; determining whether the species of the animal to be scanned is the same as the type of the animal bed; and, if yes, determining that the species of the animal to be scanned matches the type of the animal cabin, otherwise, determining that the species of the animal to be scanned does not match the type of the animal cabin.

Specifically, in this embodiment, the animal cabins include cabins for different species of animals, such as a mouse cabin, a rat cabin, and a rabbit cabin. An animal cabin may also contain multiple animal beds, for example, a single-mouse cabin, a two-mice cabin, a four-mice cabin, a single-rat cabin, a two-rats cabin, or a single-rabbit cabin.

Figure 6:
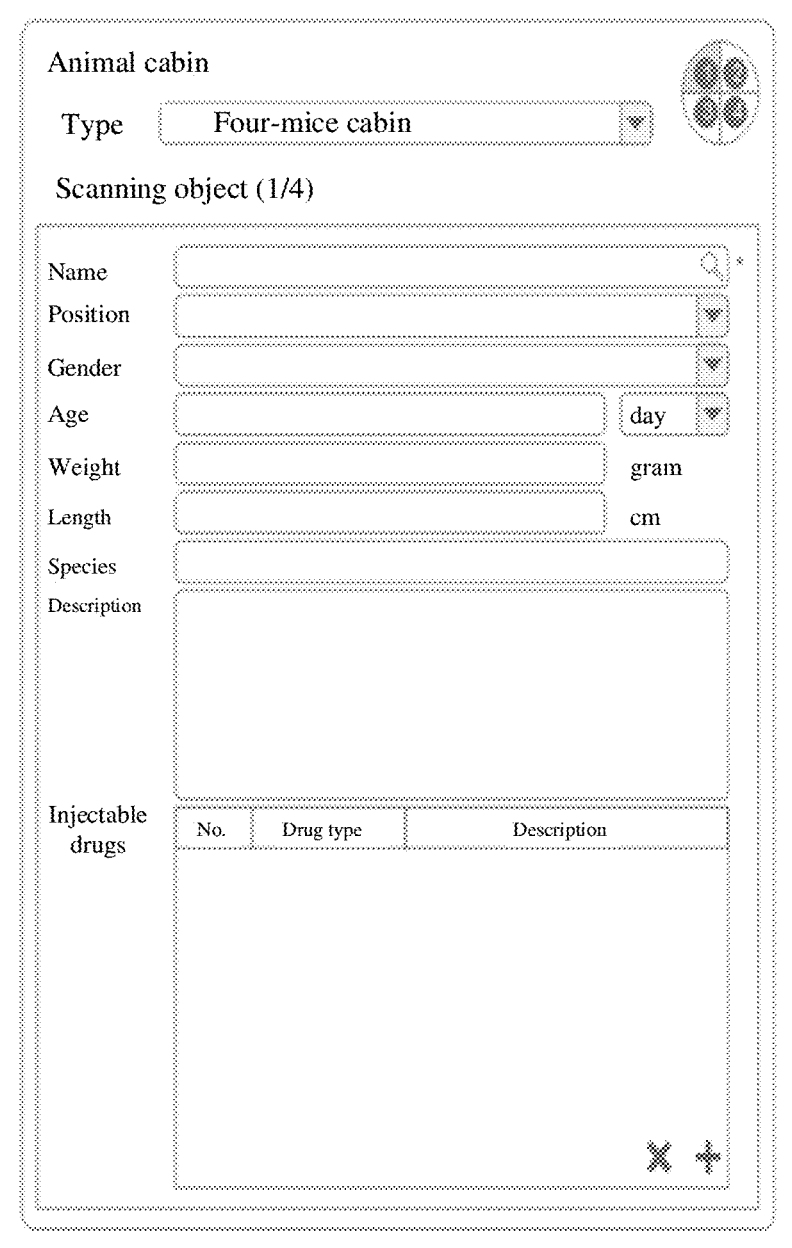

After the type of the animal cabin is detected, the registration page is dynamically set according to the number of beds to guide the user to enter the registration information. The registration information of each scanned object can be entered for the implementation of the subsequent scanning process. After the type of the animal cabin is detected, the animal cabin model is displayed, and the user selects different beds to enter the registration information of the corresponding scanning object. Specifically, as shown in FIG. 6, an animal cabin (four-mice animal cabin) in which four mice can be placed is detected at a workstation, and the registration page displays four beds, i.e., the circular icon with the number "1, 2, 3, 4" in the upper right corner as shown in FIG. 6. The user can click the corresponding number in the circular icon to enter the registration information of the animal to be scanned in the corresponding bed. After the registration information is entered, the registration information is automatically verified to determine whether all the required registration information has been entered. If not, a supplementary entry prompt will be given. Alternatively, the basic registration information of the scanned object includes, but is not limited to, name, position, gender, age, weight, length, species, and description. Registration information for injectable drugs includes, but is not limited to, drug name, nuclide, dose, injection date, and injection time.

For the multi-bed animal cabin, the occupancy of each bed is determined before the registration information is entered, and the bed is set to an unused state or a used state according to the occupancy of the bed. If one or more beds in the multi-bed animal cabin do not have a scanning object placed, the bed(s) can be set to the unused state on the registration page. When a certain bed is set to the unused state, the scanning object information corresponding to the unused bed will not be checked when the registration system verifies the required registration information.

The determination of the occupancy of the bed can also be made according to the corresponding physiological signals at the bed and/or the corresponding images, and the determination can be made by referring to an animal survival determination mode. For example, if the physiological signal does not exist and the animal to be scanned is not recognized in the image, the animal is determined not to be placed in the scanning area, i.e., the bed is in the unused state. If the physiological signal exists and the animal to be scanned can be identified in the image, the animal is determined to have been put into the scanning area and is alive, i.e., the bed is in the used state. If the physiological signal does not exist, but the animal to be scanned can be recognized in the image, the animal is determined to be dead, which means that the bed is in the used state, but the scanning cannot be performed and the animal needs to be replaced.

In this embodiment, obtaining the occupancy of each animal bed in the animal cabin is relatively simple, so that the species of the animal to be scanned on the animal bed in the used state can be quickly identified. The species of the animal to be scanned on the occupied animal bed can be quickly identified so as to quickly determine whether the species of the animal to be scanned and the types of the animal bed are the same, i.e., the matching result of the species of the animal to be scanned and the type of the animal cabin can be quickly obtained, and the efficiency of obtaining the matching result of the species of the animal to be scanned and the type of the animal cabin can be improved.

Figure 7:
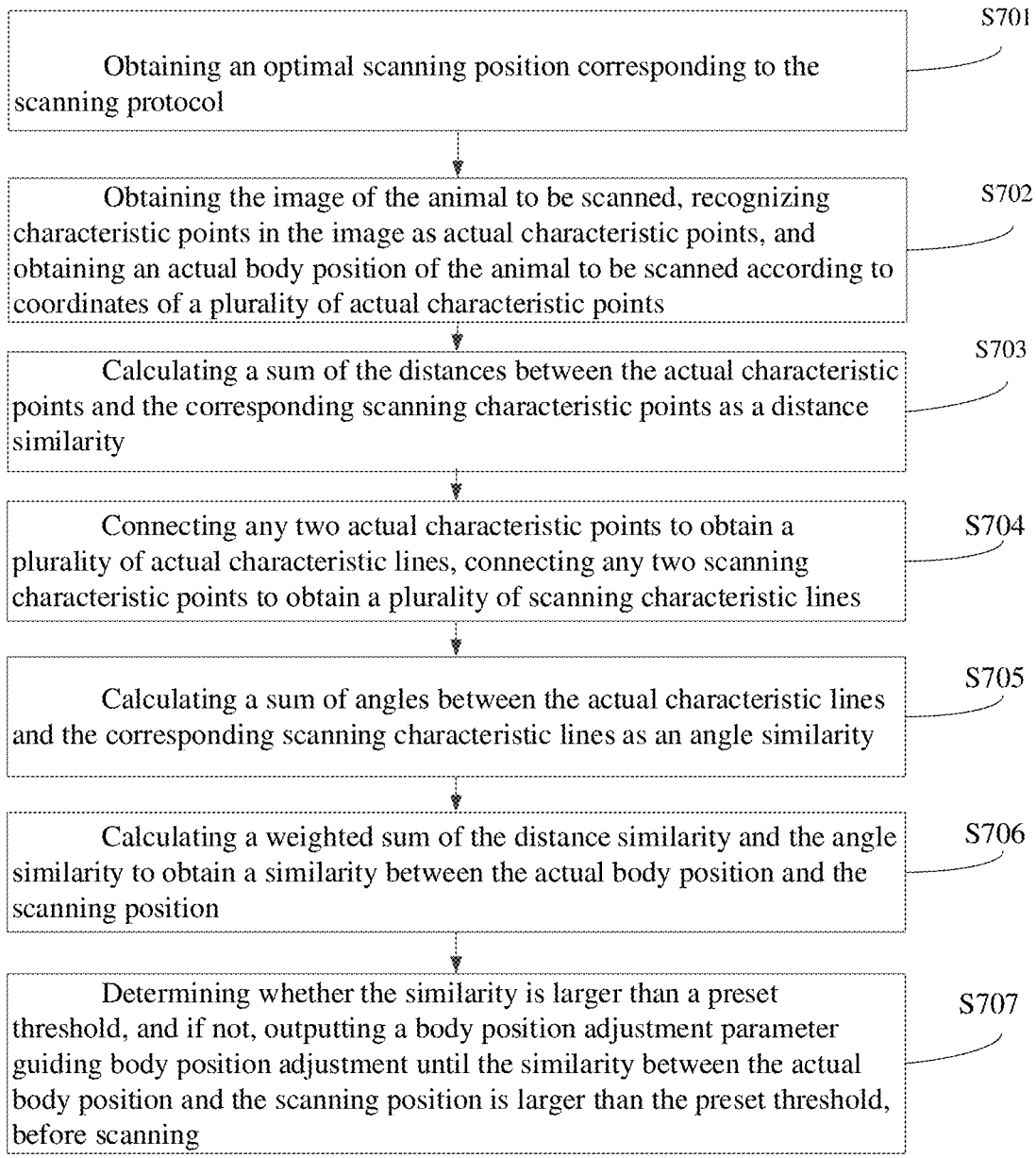
FIG. 7 is a schematic flow chart of a method for scanning an animal according to some embodiments of the present application.

In some embodiments, as shown in FIG. 7, the method for scanning an animal includes, prior to scanning according to a corresponding scanning protocol as described above, or according to a user-defined scanning protocol, following steps S701-S707.

In the step S701, an optimal scanning position corresponding to the scanning protocol is obtained.

Specifically, the scanning device obtains the optimal scanning position corresponding to the scanning protocol according to scanning positions corresponding to the scanning protocol. Alternatively, the scanning device may determine the optimal scanning position corresponding to the scanning protocol among a plurality of scanning positions corresponding to the scanning protocol.

In the step S702, the image of the animal to be scanned is obtained, characteristic points in the image are recognized as actual characteristic points, and the coordinates of a plurality of actual characteristic points are combined to obtain an actual body position of the animal to be scanned.

Specifically, in the present embodiment, the actual body position is described using characteristic points. The type of the characteristic points describing the body position can be selected and set according to the characteristics of the animal to be scanned and the characteristics of the scanning area. The characteristic points include characteristic points that describe positions and characteristic points that describe directions. For example, when the head of a mouse needs to be scanned, the eye of the mouse can be selected as a characteristic point to describe the position of the head, and then the ear and the eye are selected to jointly describe the direction of the head, so that the position and direction of the mouse head can be comprehensively fixed, and the body position of the mouse head can be accurately described. The scanning position corresponding to the scanning protocol includes scanning characteristic points in one-to-one correspondence with the plurality of actual characteristic points.

In the step S703, a sum of the distances between the actual characteristic points and the corresponding scanning characteristic points is calculated as a distance similarity.

It should be noted that in an embodiment of the present application, when calculating distance similarity, the sum of the distances of all characteristic points is not calculated, but the sum of the distances corresponding to the characteristic points describing the position is calculated, so that not only the computation amount is reduced, but also the impact of the undesired characteristic points describing the direction on the distance similarity calculation is eliminated.

In the step S704, any two actual characteristic points are connected to obtain a plurality of actual characteristic lines, and any two scanning characteristic points are connected to obtain a plurality of scanning characteristic lines.

In the step S705, a sum of angles between the actual characteristic lines and the corresponding scanning characteristic lines is calculated as an angle similarity.

It should be noted that when calculating the angle similarity, the actual characteristic line and the scanning characteristic line describing the direction are constructed, and then only the sum of the angles between the actual characteristic line describing the direction and the corresponding scanning characteristic line is calculated as the angle similarity, so as to quickly and accurately calculate the angle similarity.

In the step S706, a weighted sum of the distance similarity and the angle similarity is calculated to obtain a similarity between the actual body position and the scanning position.

Specifically, when calculating the similarity between the actual body position and the scanning position, the embodiment takes into account the impact of two aspects, i.e., position (including distance) and direction (including angle), so that the calculated similarity can describe the differences between the actual body position and the scanning position from two aspects. The embodiment ensures that the actual body position and the scanning position can reach a required similarity in both aspects before scanning.

Figure 8:
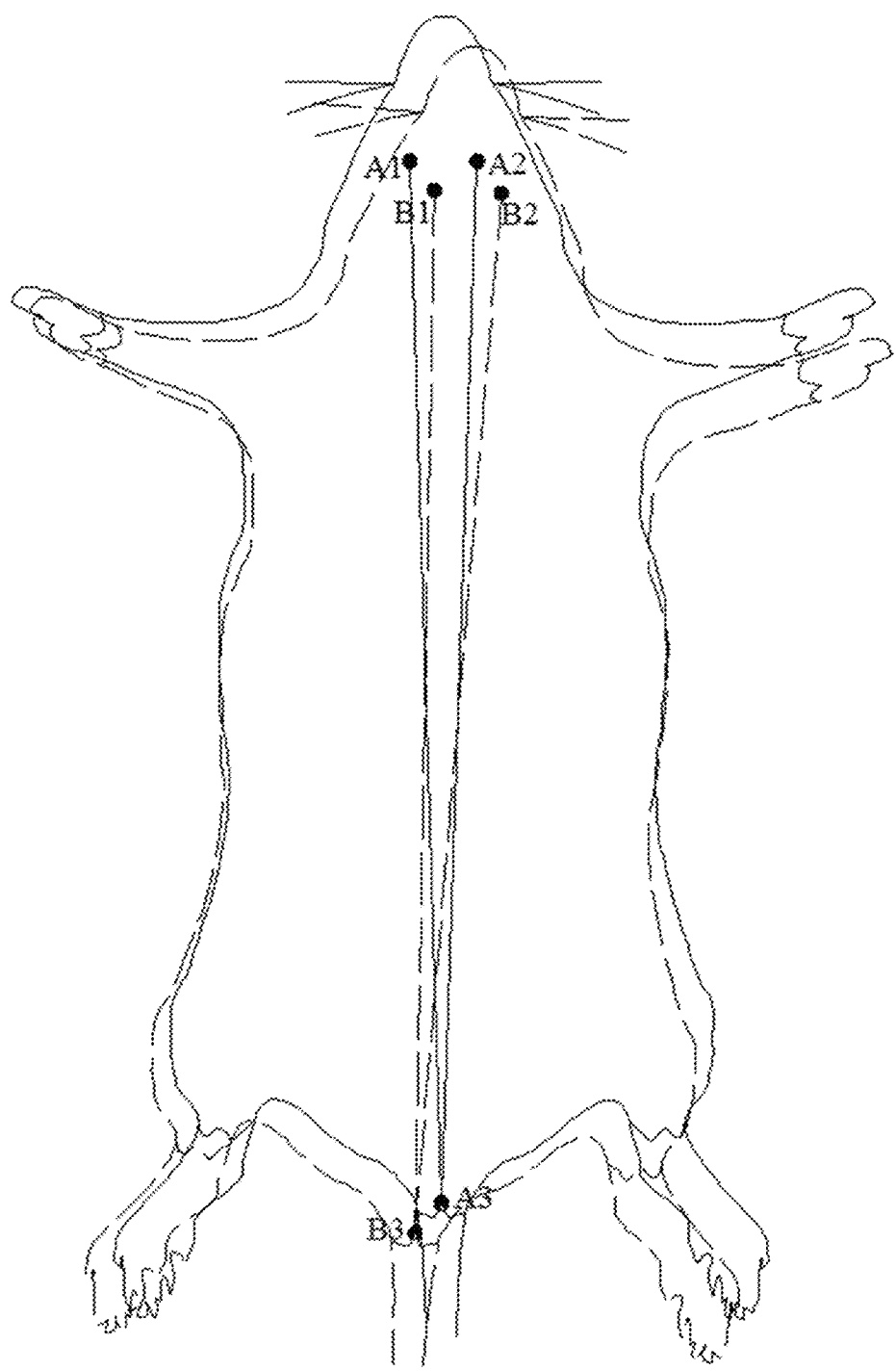
FIG. 8 is a schematic diagram of similarity calculation for a method for scanning an animal according to some embodiments of the present application.

For example, when scanning a mouse head, the sum of the distances corresponding to the characteristic points of two eyes can be taken as the distance similarity, the lines between two eyes and the intersection of the tail and body are selected as the characteristic lines, and the sum of the angles corresponding to the two characteristic lines is taken as the angle similarity. Exemplarily, as shown in FIG. 8, the solid line in FIG. 8 shows the scanning position of the mouse, and the dotted line shows the actual position of the mouse. Points A1, A2, and A3 are scanning characteristic points, A1 and A2 are the eyes of the mouse, and A3 is the intersection of the tail and the body of the mouse. Points B1, B2, and B3 are all actual characteristic points, B1, B2 are the eyes of the mouse, and B3 is the intersection of the tail and the body of the mouse. The distance AB1 between the scanning characteristic point A1 and the actual characteristic point B1 is calculated, the distance AB2 between the scanning characteristic point A2 and the actual characteristic point B2 is calculated, and AB1+AB2 is taken as the distance similarity. A1 and A3 are connected to obtain a first scanning characteristic line, A2 and A3 are connected to obtain a second scanning characteristic line, B1 and B3 are connected to obtain a first actual characteristic line, and B2 and B3 are connected to obtain a second actual characteristic line. The angle values between the first scanning characteristic line and the first actual characteristic line and the angle value between the second scanning characteristic line and the second actual characteristic line are calculated and the sum of the two angle values is taken as the angle similarity.

Alternatively, a distance weight and an angle weight can be set according to the species of the animal to be scanned and the requirements for the position and direction in the scanning area, and the sum of the distance weight and angle weight is equal to one.

In the step S707, whether the similarity is larger than a preset threshold is determined. If not, a body position adjustment parameter guiding body position adjustment is output until the similarity between the actual body position and the scanning position is larger than the preset threshold, before scanning.

Specifically, after calculating the weighted sum of the distance similarity and the angle similarity to obtain the similarity, the similarity is compared with the preset threshold. The preset threshold is set according to the specific requirements. The preset threshold is set to 1 in this embodiment. Outputting a body position adjustment parameter guiding body position adjustment includes outputting the distance between each actual characteristic point and the corresponding scanning characteristic point and the angle between each actual characteristic line and the corresponding scanning characteristic line, as body position adjustment parameters.

Specifically, when outputting the body position adjustment parameters, it is not necessary to output all distance parameters and all angle parameters. Only the distances corresponding to the characteristic points describing the position and the angles corresponding to the characteristic lines describing the direction need to be output as body position adjustment parameters. When adjusting the position of the animal according to the body adjustment parameters, the adjustment can be made manually or automatically. For example, after an animal bed having an adjustment mechanism is set and the animal is fixed on the bed by a fixing assembly, the parameters of the adjustment mechanism are adjusted according to the body adjustment parameters, and the body position of the animal is automatically adjusted. The adjusting mechanism includes a rotating mechanism and a translation mechanism. The rotating mechanism is connected with a corresponding fixing assembly and drives the corresponding fixing assembly to rotate so as to adjust the direction of the scanning area of the animal to be scanned. The translation mechanism is connected with a corresponding fixing assembly and drives the corresponding fixing assembly to move so as to adjust the position of the scanning area of the animal to be scanned.

In this embodiment, when calculating the similarity between the actual body position and the scanning position, the impact of the position (including distance) and the direction (including angle) is taken into consideration, so that the calculated similarity can describe the differences between the actual body position and the scanning position from two aspects, and then whether the similarity is greater than the preset threshold value can be determined. When the similarity is less than the preset threshold, the body position adjustment parameters are outputted to guide the body position adjustment until the similarity between the actual body position and the scanning position is larger than the preset threshold, and then the scanning is performed. It is thus ensured that the actual body position and the scanning position reach a required similarity in the two aspects before scanning.

Figure 9:
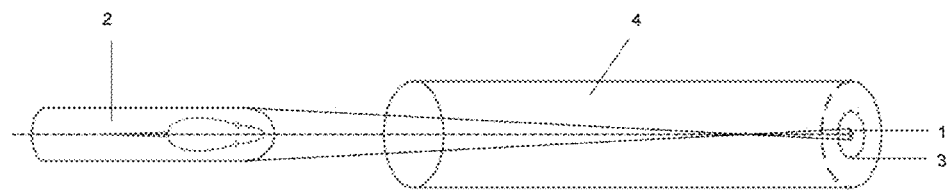
FIG. 9 is a schematic view of the structure of a video monitoring system of an animal imaging device according to some embodiments of the present application.

In some embodiments of the present application, cameras are provided on the animal cabin and/or on the animal imaging device body. The image of the animal to be scanned is obtained through the camera. The camera can be arranged on the animal cabin, on the animal imaging device body, or on the animal cabin and the animal imaging device body at the same time. It is to be understood that the camera being arranged on the animal cabin includes the camera being arranged inside the animal cabin or on an outer surface of the animal cabin, as long as the image of the animal to be scanned inside the animal cabin can be obtained by the camera attached to the animal cabin structure. The camera being arranged on the animal imaging device body includes the camera being arranged on an outer surface of the animal imaging device body or inside a scanning hole of the animal imaging device body. It should be understood that a plurality of cameras may be provided and the plurality of cameras are distributed on the animal cabin and/or on the animal imaging device body. To obtain the image of the animal to be scanned, the camera needs to be focused, and the image of the animal to be scanned is obtained under the condition that the camera is focused. In an embodiment, as shown in FIG. 9, the animal imaging device body 4 is provided with a camera 1 which can be a monitoring camera. The method for scanning an animal includes obtaining a distance between the animal cabin 2 and the camera 1, and adjusting the focal length of the camera 1 according to the distance to realize the focusing of the camera.

It will be appreciated that when an animal imaging device is operating, a monitoring device, i.e., a camera in the embodiments of the present application, is integrated on the animal imaging device in order to facilitate the observation of animal conditions by an experimenter. The cameras are configured for real-time observation of animals undergoing experiments. The camera is arranged on the animal imaging device body. The initial position of the animal cabin is positioned outside the animal imaging device and can be driven and pushed into the animal imaging device body so as to enable the animal imaging device to scan the animal in the animal cabin. When the camera monitors the animal, in order to ensure the clarity of the monitoring video, the camera needs to have a suitable focal length in order to obtain a suitable image. Based on the optical principle, the focal length of the camera is related to the distance between the camera and the object to be photographed and the image distance of the camera. In an embodiment of the present application, the focal length of the camera is adjusted in real time by obtaining the distance between the camera and the animal cabin. The camera is a zoomable optical camera. Specifically, the scanning device obtains the distance between the animal cabin and the camera, adjusts the focal length of the camera according to the distance between the animal cabin and the camera, and realizes the focusing of the camera.

In an embodiment, the scanning device obtains the distance between the animal cabin and the camera by following steps A-C.

In the step A, an initial distance between the animal cabin and the camera is obtained.

In the step B, real-time data of an encoder of the driving device of the animal cabin is obtained and a real-time travel distance of the animal cabin is obtained according to the real-time data of the encoder. The driving device of the animal cabin is configured to drive the animal cabin to move.

In the step C, a real-time distance between the animal cabin and the camera is calculated according to the initial distance and the real-time travel distance.

In some embodiments, after an animal imaging experiment, the animal cabin is reset (restoring the animal cabin to its initial position). The initial position of the animal cabin before performing the animal imaging experiments is a preset position, and the position of the camera is fixed. The initial distance between the animal cabin and the camera is certain and can be directly obtained through the installation parameters for installation, which is simple and convenient. In this embodiment, when animal scanning is required, the animal cabin slowly approaches the animal imaging device body, and the real-time travel distance of the animal cabin is the travel distance of the animal cabin from the initial position. The animal cabin is driven by the driving device. The encoder is arranged on the driving device, so the data of the encoder reflects the movement data of the driving device, and the movement data of the driving device corresponds to the travel distance of the animal cabin in real time.

In an embodiment of the present application, alternatively, a method of obtaining the real-time travel distance of the animal cabin includes obtaining the real-time data of the encoder of the driving device of the animal cabin and obtaining the travel distance of the animal cabin according to the real-time data of the encoder. The driving device of the animal cabin is configured to drive the animal cabin to move. Alternatively, in this embodiment, the driving device is an electric motor.

In an embodiment of the present application, when the initial distance between the animal cabin and the camera and the real-time travel distance of the animal cabin are determined, the real-time distance between the animal cabin and the camera can be calculated according to the kinematics principle. Specifically, the real-time distance between the animal cabin and the camera is calculated by calculating the difference between the initial distance between the animal cabin and the camera and the real-time travel distance of the animal cabin, and taking the difference as the real-time distance between the animal cabin and the camera.

In this embodiment, the animal cabin moves close to the camera, so the real-time distance between the animal cabin and the camera is the initial distance minus the real-time travel distance. It should be understood that, in other embodiments, the camera may be disposed on the side of the animal cabin away from the animal imaging apparatus body, and the real-time distance between the camera and the animal cabin is the sum of the initial distance and the real-time travel distance. Thus, the specific calculation method of the real-time distance depends on the position of the camera, which is not limited by the present application. It should be understood that, regardless of the location of the camera, the calculation of the real-time distance should be related to the initial distance of the animal cabin from the camera and the real-time travel distance of the animal cabin.

Figure 10:
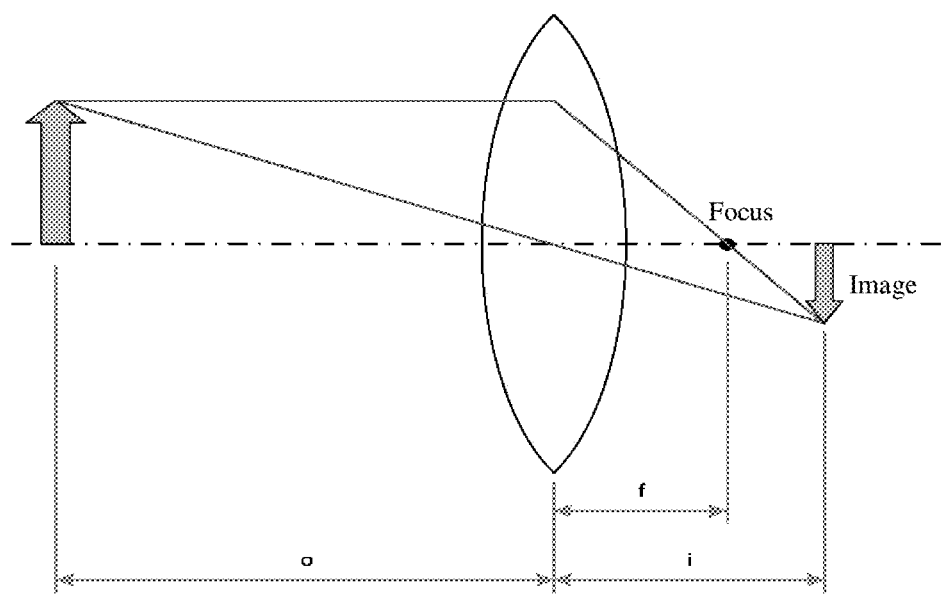
FIG. 10 is a schematic diagram of a physical model of camera lens imaging according to some embodiments of the present application.

Further, after obtaining the real-time distance between the animal cabin and the camera, the target focal length of the camera can be calculated according to the real-time distance and the image distance of the camera, and the real-time focal length of the camera can be adjusted according to the target focal length to realize focusing of the camera. Specifically, the image distance of the camera is a fixed parameter, and the object distance of the camera varies with the real-time travel distance of the animal cabin and is linear. The object distance of the camera can be directly calculated through the obtained real-time travel distance of the animal cabin, and the focal length can be calculated according to the lens imaging formula after the object distance is obtained. It should be noted that in this embodiment, the real-time distance is the distance between the imaging point of the camera and a certain fixed point of the animal cabin. In an embodiment, for convenience of measurement, the fixed point is the front end of the animal cabin. It should be understood that, in other embodiments, the fixed point can also be a point from the rear end or the middle of the animal cabin. Exemplarily, in an embodiment of the present application, the distance between a front end of the animal cabin in a forward direction and the camera is denoted by $l_0$, and the travel distance of the animal cabin is denoted by d, the real-time distance between the front end of the animal cabin and the imaging point of the camera is denoted by $l_0-d$. Also referring to FIG. 10, which is a physical model diagram of lens imaging of a camera in an embodiment, it can be seen from FIG. 8 that by denoting the image distance of the camera by i, the object distance of the camera is $o=l_0-d-i$. According to the lens imaging equation $$\frac{1}{o} + \frac{1}{f} = \frac{1}{i},$$

the calculation of the target focal length of the camera is:

$$f = \frac{1}{\frac{1}{i} - \frac{1}{o}}$$

where f denotes the target focal length of the camera, i denotes the imaging distance of the camera, and o denotes the object distance of the camera. Therefore, when performing an animal scanning experiment, the target focal length of the camera can be quickly calculated according to the equation by monitoring the travel distance of the animal cabin in real time, which is simple and convenient. Furthermore, because the camera is a zoomable optical camera, it only needs to zoom according to the target focal length, which ensures that the camera can capture a clear image without additional distance measurement, and the system is simple and accurate.

In this embodiment, by obtaining the distance between the animal cabin and the camera, the focal length of the camera can be adjusted according to the distance between the animal cabin and the camera, so that the focus of the camera can be realized, and a clear image can be taken by the camera when the camera is focused.

In addition, it should be noted that based on focusing method for the monitoring camera of the animal imaging device, the monitoring camera can also be used to monitor the animal to be scanned in real time, so that the operators can obtain the conditions of the animal in the animal cabin in real time.

It should be understood that although the steps in the flow charts in FIGS. 2-7 are shown sequentially as indicated by the arrows, these steps are not necessarily performed sequentially as indicated by the arrows. Unless specifically stated herein, the execution of these steps is not strictly limited in order, and these steps may be performed in other orders. Moreover, at least a portion of the steps in FIGS. 2-7 may include a plurality of steps or stages that may not necessarily be performed at the same time, but may be performed at different times, and the steps or stages may not necessarily be performed sequentially, but may be performed alternately with other steps, steps or stages of the other steps, or at least a portion of the steps or stages of the other steps.

Figure 11:
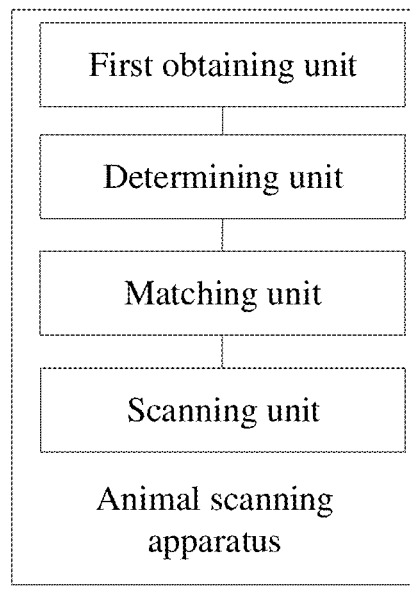
FIG. 11 is a block diagram of a structure of an animal scanning apparatus according to some embodiments of the present application.

In an embodiment, shown in FIG. 11, an animal scanning apparatus is provided, which includes a first obtaining unit, a determination unit, a matching unit and a scanning unit.

The first obtaining unit is configured for obtaining a species of the animal to be scanned.

The determining unit is configured for identifying a type of an animal cabin where the animal to be scanned is located and determining whether the species of the animal to be scanned matches the type of the animal cabin.

The matching unit is configured for determining and presenting a corresponding scanning protocol that matches the species of the animal to be scanned if the species of the animal to be scanned matches the type of the animal cabin.

The scanning unit is configured for performing a scan according to the corresponding scanning protocol or according to a user-defined scanning protocol.

The animal scanning apparatus provided by the embodiments can perform the method as described above in the embodiments, and the implementation and technical effect thereof are similar, and are not described again here.

Based on the above embodiments, the above apparatus further includes a second obtaining unit and a third obtaining unit.

The second obtaining unit is configured for obtaining an image of the animal to be scanned.

The third obtaining unit is configured for obtaining the species of the animal to be scanned according to the images of the animal to be scanned, and/or monitoring the animal to be scanned according to the image of the animal to be scanned.

The animal scanning apparatus provided by this embodiment can perform the method as described above in the embodiments, and the implementation and technical effect thereof are similar, and are not described again here.

Based on the above embodiments, the above apparatus further includes a first determination unit.

The first determining unit is configured for determining whether the user-defined scanning protocol matches the species of the animal to be scanned or not, and if not, prompting to modify the user-defined scanning protocol.

The animal scanning apparatus provided by the embodiment can perform the method as described above in the embodiments, and the implementation and technical effect thereof are similar, and are not described again here.

Based on the above embodiments, the above apparatus further includes a second determination unit.

The second determining unit is configured for obtaining physiological signals and a real-time image of the animal to be scanned, and determining whether the animal to be scanned is alive according to the physiological signals and the real-time image. If not, an animal sample change reminder is output.

The animal scanning apparatus provided by the embodiment can perform the method as described above in the embodiments, and the implementation and technical effect thereof are similar, and are not described again here.

Based on the above examples, the first obtaining unit is configured for setting physiological signal ranges for different species of animals, establishing a physiological signal database, and matching the animal species corresponding to the physiological signals in the physiological signal database to obtain the species of the animal to be scanned.

The animal scanning apparatus provided by the embodiment can perform the method as described above in the embodiments, and the implementation and technical effect thereof are similar, and are not described again here.

Based on the above embodiments, the first obtaining unit is configured for obtaining a body length parameter of the animal by recognizing the image, obtaining a weight parameter of the animal to be scanned, comparing the obtained body length parameter and the obtained body weight parameter with pre-stored standard body lengths and standard body weights respectively, and determining the animal species information.

The animal scanning apparatus provided by the embodiment can perform the method as described above in the embodiments, and the implementation and technical effect thereof are similar, and are not described again here.

Based on the above embodiments, the above apparatus further includes a fourth obtaining unit.

The fourth obtaining unit is configured for, after obtaining the image of the animal to be scanned, obtaining a hair parameter of the animal, and determining the animal species information according to the hair parameter, the body length parameter, and the weight parameter of the animal. The hair parameter includes at least one of a hair length, a hair diameter, and a hair color.

The animal scanning apparatus provided by the embodiment can perform the method as described above in the embodiments, and the implementation and technical effect thereof are similar, and are not described again here.

Based on the above embodiments, the first obtaining unit is configured for providing a ruler with markings on either side of the animal and obtaining the body length parameter by recognizing the markings of the ruler, and/or marking characteristic points on an animal body and determining the body length parameter by recognizing the characteristic points.

The animal scanning apparatus provided by the embodiment can perform the method as described above in the embodiments, and the implementation and technical effect thereof are similar, and are not described again here.

Based on the above examples, the first obtaining unit is configured for obtaining a plurality of body weight values of the animal to be scanned and obtaining the weight parameter of the animal to be scanned based on the plurality of weight values.

The animal scanning apparatus provided by the embodiment can perform the method as described above in the embodiments, and the implementation and technical effect thereof are similar, and are not described again here.

Based on the above embodiments, the above apparatus further includes an identification unit.

The identification unit is configured for determining whether a specified part of an animal body is shaved or not and whether an electrode sheet is attached to the specified part according to the image of the animal to be scanned to select a respiratory-electrocardiogram protocol.

The animal scanning apparatus provided by the embodiment can perform the method as described above in the embodiments, and the implementation and technical effect thereof are similar, and are not described again here.

Based on the above embodiments, alternatively, the type of the animal cabin involves a type of corresponding animal beds and a number of the animal beds, and the determination unit is configured for obtaining an occupancy of each animal bed in the animal cabin, identifying the species of the animal to be scanned on the occupied animal bed, determining whether the species of the animal to be scanned is the same as the type of the animal bed, and if yes, determining that the species of the animal to be scanned matches the type of the animal cabin, otherwise, determining that the species of the animal to be scanned does not match the type of the animal cabin.

The animal scanning apparatus provided by the embodiment can perform the method as described above in the embodiments, and the implementation and technical effect thereof are similar, and are not described again here.

Based on the above embodiments, alternatively, the above apparatus further includes a fifth obtaining unit, a sixth obtaining unit, a first calculating unit, a seventh obtaining unit, a second calculating unit, a third calculating unit, and a third determination unit.

The fifth obtaining unit is configured for obtaining an optimal scanning position corresponding to the scanning protocol.

The sixth obtaining unit is configured for obtaining the image of the animal to be scanned, recognizing characteristic points in the image as actual characteristic points, and obtaining an actual body position of the animal to be scanned according to coordinates of a plurality of actual characteristic points. The scanning position includes scanning characteristic points in one-to-one correspondence with the plurality of actual characteristic points.

The first calculating unit is configured for calculating a sum of the distances between the actual characteristic points and the corresponding scanning characteristic points as a distance similarity.

The seventh obtaining unit is configured for connecting any two actual characteristic points to obtain a plurality of actual characteristic lines and connecting any two scanning characteristic points to obtain a plurality of scanning characteristic lines.

The second calculating unit is configured for calculating a sum of angles between the actual characteristic lines and the corresponding scanning characteristic lines as an angle similarity.

The third calculating unit is configured for calculating a weighted sum of the distance similarity and the angle similarity to obtain a similarity between the actual body position and the scanning position.

The third determining unit is configured for determining whether the similarity is larger than a preset threshold, and if not, outputting a body position adjustment parameter guiding body position adjustment until the similarity between the actual body position and the scanning position is larger than the preset threshold, before scanning.

The animal scanning apparatus provided by the embodiment can perform the method as described above in the embodiments, and the implementation and technical effect thereof are similar, and are not described again here.

Based on the above embodiments, alternatively, the above apparatus further includes an eighth obtaining unit.

The eighth obtaining unit is configured for obtaining the distance between the animal cabin and the camera, and adjusting the focal length of the camera according to the distance to realize the focusing of the camera.

The animal scanning apparatus provided by the embodiment can perform the method as described above in the embodiments, and the implementation and technical effect thereof are similar, and are not described again here.

Based on the above embodiments, alternatively, the eighth obtaining unit is configured for obtaining an initial distance between the animal cabin and the camera, obtaining real-time data of an encoder of the driving device of the animal cabin and obtaining a real-time travel distance of the animal cabin according to the real-time data of the encoder. The driving device of the animal cabin is configured for driving the animal cabin to move. The real-time distance between the animal cabin and the camera is calculated according to the initial distance and the real-time travel distance.

The animal scanning apparatus provided by the embodiment can perform the method as described above in the embodiments, and the implementation and technical effect thereof are similar, and are not described again here.

Specific limitations regarding the animal scanning apparatus can be found in the foregoing limitations regarding the method of scanning an animal, which is not repeated herein. Each unit in the animal scanning apparatus may be implemented in whole or in part by software, hardware, and combinations thereof. The aforementioned units may be embedded in hardware or independently of the processor in the computer device, or may be stored in software in memory in the computer device so that the processor can call to perform operations corresponding to each of the above units.

Figure 12:
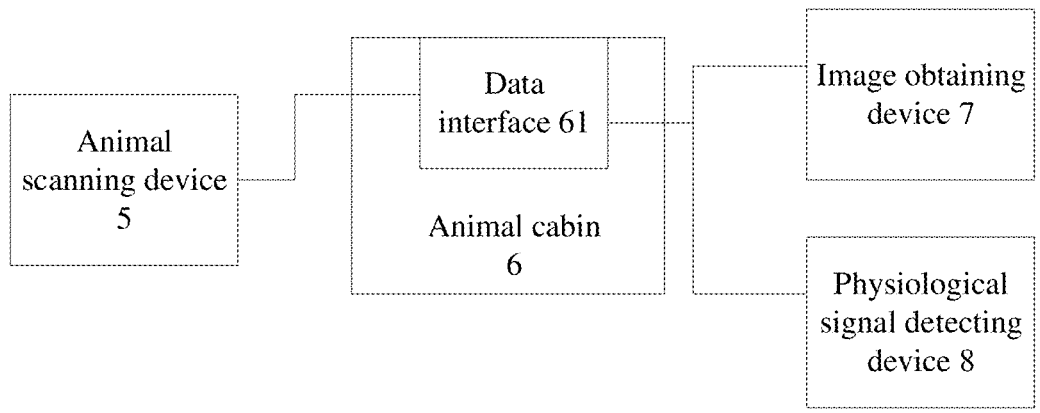
FIG. 12 is a block diagram of an animal scanning system according to some embodiments of the present application.

In an embodiment, shown in FIG. 12, an animal scanning system is provided, including an animal scanning apparatus 5 as described in any of the embodiments described above. The system further includes an animal cabin 6, an image obtaining device 7, and a physiological signal detecting device 8.

The animal cabin 6 is arranged on the bed body and is configured for placing the animal to be scanned.

The image obtaining device 7 is configured for obtaining an image of the animal to be scanned.

The physiological signal detecting device 8 is configured for obtaining a physiological signal of the animal to be scanned.

The animal scanning apparatus 5 is configured for scanning the animal to be scanned.

In some embodiments, a scanning bed is provided in the animal cabin, and the animal to be scanned may be fixed to the scanning bed. The image obtaining apparatus may include a camera as described in any of the above embodiments for capturing an image of the animal to be scanned. The physiological signal detecting device is set according to the physiological signals to be detected. For example, if an animal heartbeat needs to be detected, an electrocardiogram monitor is used. The animal cabin has a data interface for transmitting images and physiological signals to the animal scanning apparatus. The animal scanning apparatus receives the various signals and realizes scanning by performing the method for scanning an animal provided by the present application.

The animal scanning system provided in some embodiments of the present application can perform the method as described above in the embodiments, and the implementation and technical effect thereof are similar, and are not described again here.

Based on the above embodiments, alternatively, the animal scanning system includes a light source and an animal imaging device body.

The animal imaging device body is provided with a scanning hole, and the animal cabin can move along an axial direction of the scanning hole. The light source is fixedly arranged on the animal imaging device body. In an embodiment, the light source rotates with the camera through the autofocus of the camera, providing the necessary light for the camera to capture the image of the animal.

In this embodiment, the animal imaging device body may be a frame of an animal imaging device. In some embodiments of the present application, the animal imaging device is a device for scanning imaging of an animal, including CT, MR, SPECT, PET and a combination of two or more modes.

The animal scanning system provided in the embodiment can perform the method as described above in the embodiments, and the implementation and technical effect thereof are similar, and are not described again here.

Based on the above embodiments, the image obtaining device is alternatively arranged on the animal cabin and/or on the animal imaging device body.

The animal scanning system provided by the embodiment can perform the method as described above in the embodiments, and the implementation and technical effect thereof are similar, and are not described again here.

Finally, it should be noted that relational terms such as "first" and "second" are only used to differentiate an entity or operation from another entity or operation in this specification, and do not require or imply any real relationship or sequence among these entities or operations. Furthermore, terms "include", "contain" or any of their derivatives are intended to convey a non-exclusive connotation, so that a process, a method, an article or a device including a series of elements not only includes such elements, but also includes other elements that are not listed explicitly, or further includes inherent elements of the process, the method, the article or the device. If no more limitations are made, an element limited by "include a/an . . . " does not exclude another same element existing in the process, the method, the article, or the device that includes the element.

The various embodiments of the present specification are described in a progressive manner, and each embodiment highlights differences from other embodiments. The same or similar portions of the various embodiments can be referred to each other.

The embodiments disclosed above are described to enable a person skilled in the art to implement or use the present disclosure. Various modifications to the embodiments are obvious to the person skilled in the art, and general principles defined in this specification may be implemented in other embodiments without departing from the scope of the present disclosure. Therefore, the present disclosure will not be limited to the embodiments described in this specification but extends to the widest scope that complies with the principles and novelty disclosed in this specification.

What is claimed is:

1. A method for scanning an animal, comprising:
   obtaining a species of an animal to be scanned;
   identifying a type of an animal cabin where the animal to be scanned is located, and determining whether the species of the animal to be scanned matches the type of the animal cabin;
   determining and presenting a corresponding scanning protocol that matches the species of the animal to be scanned if the species of the animal to be scanned matches the type of the animal cabin; and
   performing a scan according to the corresponding scanning protocol, or according to a user-defined scanning protocol.

2. The method according to claim 1, further comprising:
   obtaining an image of the animal to be scanned; and
   obtaining the species of the animal to be scanned according to the image of the animal to be scanned, and/or monitoring the animal to be scanned in real time according to the image of the animal to be scanned.

3. The method according to claim 1, wherein before performing the scan according to the user-defined scanning protocol, the method further comprises:
   determining whether the user-defined scanning protocol matches the species of the animal to be scanned, and if not, prompting to modify the user-defined scanning protocol.

4. The method according to claim 1, further comprising:
   obtaining a physiological signal and a real-time image of the animal to be scanned;
   determining whether the animal to be scanned is alive according to the physiological signal and the real-time image; and
   if not, outputting an animal sample change reminder.

5. The method according to claim 4, wherein the obtaining the species of the animal to be scanned comprises:
   setting physiological signal ranges for different species of animals and establishing a physiological signal database; and
   determining an animal species in the physiological signal database that matches the physiological signal, and obtaining the species of the animal to be scanned.

6. The method according to claim 2, wherein the obtaining the species of the animal to be scanned comprises:
   obtaining a body length parameter of the animal to be scanned by recognizing the image;
   obtaining a weight parameter of the animal to be scanned;
   comparing the obtained body length parameter and the obtained body weight parameter with pre-stored standard body lengths and pre-stored standard body weights respectively, and determining the species of the animal to be scanned.

7. The method according to claim 6, further comprising:
   after obtaining the image of the animal to be scanned, obtaining a hair parameter of the animal, and determining the species of the animal to be scanned according to the hair parameter, the body length parameter, and the weight parameter of the animal, the hair parameter comprising at least one of a hair length, a hair diameter, and a hair color.

8. The method according to claim 6, wherein the obtaining the body length parameter of the animal by recognizing the image comprises:
   providing a ruler with markings on either side of the animal and obtaining the body length parameter by recognizing the markings of the ruler; and/or
   marking characteristic points on an animal body of the animal to be scanned and determining the body length parameter by recognizing the characteristic points.

9. The method according to claim 6, wherein the obtaining the weight parameter of the animal to be scanned comprises:
obtaining a plurality of body weight values of the animal to be scanned; and
obtaining the body weight parameter of the animal to be scanned based on the plurality of body weight values.

10. The method according to claim 2, further comprising:
determining whether a specified part of an animal body of the animal to be scanned is shaved or not and whether an electrode sheet is attached to the specified part according to the image of the animal to be scanned to select a respiratory-electrocardiogram protocol.

11. The method according to claim 1, wherein the type of the animal cabin involves a type of corresponding animal beds and a number of the animal beds, and the identifying the type of the animal cabin where the animal to be scanned is located, and determining whether the species of the animal to be scanned matches the type of the animal cabin comprises:
obtaining an occupancy of each animal bed in the animal cabin;
identifying the species of the animal to be scanned on the occupied animal bed; and
determining whether the species of the animal to be scanned is the same as the type of the animal bed, and if yes, determining that the species of the animal to be scanned matches the type of the animal cabin, otherwise, determining that the species of the animal to be scanned does not match the type of the animal cabin.

12. The method according to claim 1, wherein before performing the scan according to the corresponding scanning protocol, or according to the user-defined scanning protocol, the method further comprises:
obtaining an optimal scanning position corresponding to the scanning protocol;
obtaining the image of the animal to be scanned, recognizing a plurality of characteristic points in the image as actual characteristic points, and obtaining an actual body position of the animal to be scanned according to coordinates of the plurality of actual characteristic points, the scanning position comprising scanning characteristic points in one-to-one correspondence with the plurality of actual characteristic points;
calculating a sum of the distances between the actual characteristic points and the corresponding scanning characteristic points as a distance similarity;
connecting any two actual characteristic points to obtain a plurality of actual characteristic lines, connecting any two scanning characteristic points to obtain a plurality of scanning characteristic lines, calculating a sum of angles between the actual characteristic lines and the corresponding scanning characteristic lines as an angle similarity;
calculating a weighted sum of the distance similarity and the angle similarity to obtain a similarity between the actual body position and the scanning position; and
determining whether the similarity is larger than a preset threshold, and if not, outputting a body position adjustment parameter guiding body position adjustment until the similarity between the actual body position and the scanning position is larger than the preset threshold.

13. The method according to claim 2, wherein before obtaining the image of the animal to be scanned, the method further comprises:
obtaining a distance between the animal cabin and a camera, and adjusting a focal length of the camera according to the distance to realize focusing of the camera.

14. The method according to claim 13, wherein the obtaining the distance between the animal cabin and the camera comprises:
obtaining an initial distance between the animal cabin and the camera;
obtaining real-time data of an encoder of a driving device of the animal cabin and obtaining a real-time travel distance of the animal cabin according to the real-time data of the encoder, the driving device of the animal cabin being configured to drive the animal cabin to move; and
calculating a real-time distance between the animal cabin and the camera according to the initial distance and the real-time travel distance.

15. An animal scanning system, comprising:
an animal cabin configured to place an animal to be scanned; and
a scanning device configured to:
obtain a species of the animal to be scanned;
identify a type of the animal cabin, and determining whether the species of the animal to be scanned matches the type of the animal cabin;
determine and present a corresponding scanning protocol that matches the species of the animal to be scanned if the species of the animal to be scanned matches the type of the animal cabin, and
perform a scan according to the corresponding scanning protocol, or according to a user-defined scanning protocol.

16. The animal scanning system according to claim 15, wherein the scanning device is configured to:
obtain an image of the animal to be scanned; and
obtain the species of the animal to be scanned according to the image of the animal to be scanned, and/or monitor the animal to be scanned in real time according to the image of the animal to be scanned.

17. The animal scanning system according to claim 15, wherein the scanning device is configured to, before performing the scan according to the user-defined scanning protocol,
determine whether the user-defined scanning protocol matches the species of the animal to be scanned, and if not, prompt to modify the user-defined scanning protocol.

18. The animal scanning system according to claim 15, wherein the scanning device is configured to:
obtain a physiological signal and a real-time image of the animal to be scanned;
determine whether the animal to be scanned is alive according to the physiological signal and the real-time image; and
if not, output an animal sample change reminder.

19. The animal scanning system according to claim 15, wherein the scanning device is configured to, before performing the scan according to the corresponding scanning protocol:
obtain an optimal scanning position corresponding to the scanning protocol;
obtain the image of the animal to be scanned, recognize a plurality of characteristic points in the image as actual characteristic points, and obtain an actual body position of the animal to be scanned according to coordinates of the plurality of actual characteristic points, the scanning position comprising scanning characteristic points in one-to-one correspondence with the plurality of actual characteristic points;

calculate a sum of the distances between the actual characteristic points and the corresponding scanning characteristic points as a distance similarity;

connect any two actual characteristic points to obtain a plurality of actual characteristic lines, connect any two scanning characteristic points to obtain a plurality of scanning characteristic lines, calculate a sum of angles between the actual characteristic lines and the corresponding scanning characteristic lines as an angle similarity;

calculate a weighted sum of the distance similarity and the angle similarity to obtain a similarity between the actual body position and the scanning position; and determine whether the similarity is larger than a preset threshold, and if not, output a body position adjustment parameter guiding body position adjustment until the similarity between the actual body position and the scanning position is larger than the preset threshold.

20. A computer device comprising a memory and a processor, the memory having a computer program stored therein, wherein the computer program, when executed by the processor, causes the processor to perform a method for scanning an animal as claimed in claim 1.

* * * * *